US009370299B2

(12) United States Patent
Haine et al.

(10) Patent No.: US 9,370,299 B2
(45) Date of Patent: Jun. 21, 2016

(54) DISPLAY ACCESSIBILITY FOR COLOR VISION IMPAIRMENT

(71) Applicants: D. Philip Haine, San Francisco, CA (US); Michael I. Almond, San Francisco, CA (US); Robert M. Cooper, Arlington, VA (US)

(72) Inventors: D. Philip Haine, San Francisco, CA (US); Michael I. Almond, San Francisco, CA (US); Robert M. Cooper, Arlington, VA (US)

(73) Assignee: SuccessFactors, Inc., San Francisco, CA (US)

( * ) Notice: Subject to any disclaimer, the term of this patent is extended or adjusted under 35 U.S.C. 154(b) by 100 days.

(21) Appl. No.: 13/896,185

(22) Filed: May 16, 2013

(65) Prior Publication Data

US 2014/0340644 A1    Nov. 20, 2014

(51) Int. Cl.
*A61B 3/02*     (2006.01)
*A61B 3/10*     (2006.01)
*A61B 3/06*     (2006.01)

(52) U.S. Cl.
CPC .. *A61B 3/066* (2013.01); *A61B 3/06* (2013.01)

(58) Field of Classification Search
CPC ............ A61B 3/02; A61B 3/032; A61B 3/06; A61B 3/066; A61B 3/022; A61B 3/0041; A61B 3/0325; G09G 5/06; G06F 19/322
USPC ................... 351/242, 246, 223, 239; 345/593
See application file for complete search history.

(56) References Cited

U.S. PATENT DOCUMENTS

| 4,966,453 | A  | * | 10/1990 | Chang et al. ................... 351/242 |
| 5,267,331 | A  |   | 11/1993 | Siwoff |
| 5,589,898 | A  | * | 12/1996 | Atkinson ....................... 351/237 |
| 5,799,292 | A  |   | 8/1998 | Hekmatpour |
| 5,946,075 | A  | * | 8/1999 | Horn .............................. 351/246 |
| 6,031,517 | A  | * | 2/2000 | Van Nes ........................ 345/600 |
| 6,210,006 | B1 | * | 4/2001 | Menozzi ................ A61B 3/032 351/242 |
| 6,278,441 | B1 |   | 8/2001 | Gouzman et al. |
| 6,309,117 | B1 | * | 10/2001 | Bunce et al. ..................... 400/61 |
| 6,362,830 | B1 |   | 3/2002 | Walraven |
| 6,591,008 | B1 |   | 7/2003 | Surve et al. |
| 6,876,369 | B2 |   | 4/2005 | Brown et al. |
| 6,931,151 | B2 |   | 8/2005 | Weast |
| 7,054,483 | B2 | * | 5/2006 | Poynter ......................... 382/162 |
| 7,124,375 | B1 |   | 10/2006 | Steele et al. |
| 7,264,356 | B2 | * | 9/2007 | Jones et al. ................... 351/242 |
| 7,320,109 | B1 |   | 1/2008 | Zeevi et al. |
| 7,333,117 | B2 |   | 2/2008 | Kim |

(Continued)

OTHER PUBLICATIONS

Neuronresearch, Jul. 2009. Detailed Interpretation of The Nagel Anomaloscope. http://web.archive.org/web/20120829095808/http://neuronresearch.net/vision/files/newnagel.htm.*

*Primary Examiner* — Bumsuk Won
*Assistant Examiner* — Collin X Beatty
(74) *Attorney, Agent, or Firm* — Klarquist Sparkman, LLP (57) ABSTRACT

Examples that increase accessibility of color vision impaired users to information on a display are provided herein. A plurality of graphical elements using a first color palette are presented. A user input indicating that the user has a color vision impairment is received. The color vision impairment can be, for example, deuteranopia, protanopia, or tritanopia. At least some of the plurality of graphical elements can be presented using a second color palette designed for users with the color vision impairment. The user input indicating that the user has a color vision impairment can be received in response to presenting a color vision impairment test to the user.

18 Claims, 12 Drawing Sheets

(7 of 12 Drawing Sheet(s) Filed in Color)

(56) References Cited

U.S. PATENT DOCUMENTS

| | | |
|---|---|---|
| 7,418,696 B2 | 8/2008 | Hawley et al. |
| 7,451,391 B1 | 11/2008 | Coleman et al. |
| 7,628,491 B2 * | 12/2009 | Kaplan ................. 351/242 |
| 7,703,026 B2 | 4/2010 | Bechtold et al. |
| 7,703,029 B2 | 4/2010 | Bozak et al. |
| 7,737,992 B2 | 6/2010 | Hong et al. |
| 7,800,825 B2 | 9/2010 | Brooks et al. |
| 7,831,931 B2 | 11/2010 | Klein et al. |
| 7,882,440 B2 | 2/2011 | Mohr |
| 7,916,152 B2 | 3/2011 | Jones et al. |
| 7,949,960 B2 | 5/2011 | Roessler et al. |
| 8,015,501 B2 | 9/2011 | Conrad et al. |
| 8,296,650 B2 | 10/2012 | Sudhi |
| 8,345,338 B2 * | 1/2013 | Jeong .............. H04N 9/68 359/222.1 |
| 8,412,694 B2 | 4/2013 | Wang et al. |
| 8,428,657 B2 * | 4/2013 | Scott ..................... 455/566 |
| 2004/0085327 A1 * | 5/2004 | Jones et al. ............. 345/591 |
| 2004/0212815 A1 | 10/2004 | Heeman et al. |
| 2004/0218451 A1 | 11/2004 | Said et al. |
| 2006/0033880 A1 * | 2/2006 | Korneluk .............. 351/242 |
| 2006/0256127 A1 * | 11/2006 | Cho et al. ............. 345/591 |
| 2007/0006043 A1 | 1/2007 | Pins |
| 2010/0185624 A1 * | 7/2010 | Wang et al. ............ 707/748 |
| 2010/0188639 A1 * | 7/2010 | Carda et al. ............ 351/242 |
| 2011/0145737 A1 | 6/2011 | Laugwitz et al. |
| 2011/0293177 A1 * | 12/2011 | Wang et al. ............ 382/167 |
| 2011/0305386 A1 * | 12/2011 | Wang et al. ............ 382/164 |
| 2012/0079451 A1 | 3/2012 | Halbedel et al. |
| 2012/0121172 A1 * | 5/2012 | Wang et al. ............ 382/165 |
| 2013/0069973 A1 * | 3/2013 | Ichikawa et al. ........ 345/593 |
| 2013/0141697 A1 * | 6/2013 | Berry et al. ............ 351/223 |
| 2015/0085258 A1 * | 3/2015 | Ichikawa et al. ........ 351/242 |

* cited by examiner

| HEX: 535300 | RGB: 84 / 84 / 0 |
| HEX: 787800 | RGB: 121 / 121 / 0 |
| HEX: A1A100 | RGB: 161 / 161 / 0 |
| HEX: CECE48 | RGB: 206 / 206 / 72 |
| HEX: E9E9B0 | RGB: 233 / 233 / 174 |
| HEX: F6F6F6 | RGB: 246 / 246 / 246 |
| HEX: D9D9EC | RGB: 217 / 217 / 236 |
| HEX: ADADD4 | RGB: 173 / 173 / 212 |
| HEX: 7777B0 | RGB: 119 / 119 / 176 |
| HEX: 34348C | RGB: 52 / 52 / 140 |
| HEX: 19194E | RGB: 25 / 25 / 75 |

| HEX: 552A32 | RGB: 85 / 42 / 50 |
| HEX: 8E4A55 | RGB: 142 / 74 / 85 |
| HEX: C37682 | RGB: 195 / 118 / 130 |
| HEX: E3B7BD | RGB: 227 / 183 / 189 |
| HEX: F8E1E4 | RGB: 248 / 225 / 228 |
| HEX: F4F4F4 | RGB: 244 / 244 / 244 |
| HEX: C8E6F8 | RGB: 200 / 230 / 248 |
| HEX: 85C5E9 | RGB: 133 / 198 / 234 |
| HEX: 3D8DB5 | RGB: 61 / 141 / 181 |
| HEX: 19607E | RGB: 25 / 96 / 126 |
| HEX: 113849 | RGB: 17 / 56 / 73 |

SOFTWARE 1180 IMPLEMENTING DESCRIBED TECHNOLOGIES

FIG. 12

DISPLAY ACCESSIBILITY FOR COLOR VISION IMPAIRMENT

BACKGROUND

There is an increasing recognition that efforts should be undertaken to accommodate individuals with disabilities and impairments. This recognition has resulted in various federal laws requiring accommodation for disabilities and impairments. For example, in the United States, Section 508 of the Rehabilitation Act, 29 U.S.C. 794d, requires that U.S. federal agencies make electronic and information technology accessible. Electronic display accessibility for color vision impaired users is conventionally addressed by ensuring that displayed information does not depend entirely on color to convey meaning. For example, explanatory text is provided in addition to color. Conventional accommodation, however, denies color vision impaired users the richness and clarity of the user experience provided to users with unimpaired color vision.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The examples described herein generally present displayed information so as to be more readily accessible to color vision impaired users. Upon receiving an indication that a user is color vision impaired, a color palette can be selected for a plurality of graphical elements that is associated with increased accessibility by color vision impaired users (sometimes referred to as "color blind" users). Examples are described below with reference to FIGS. 1-12.

Figure 1:
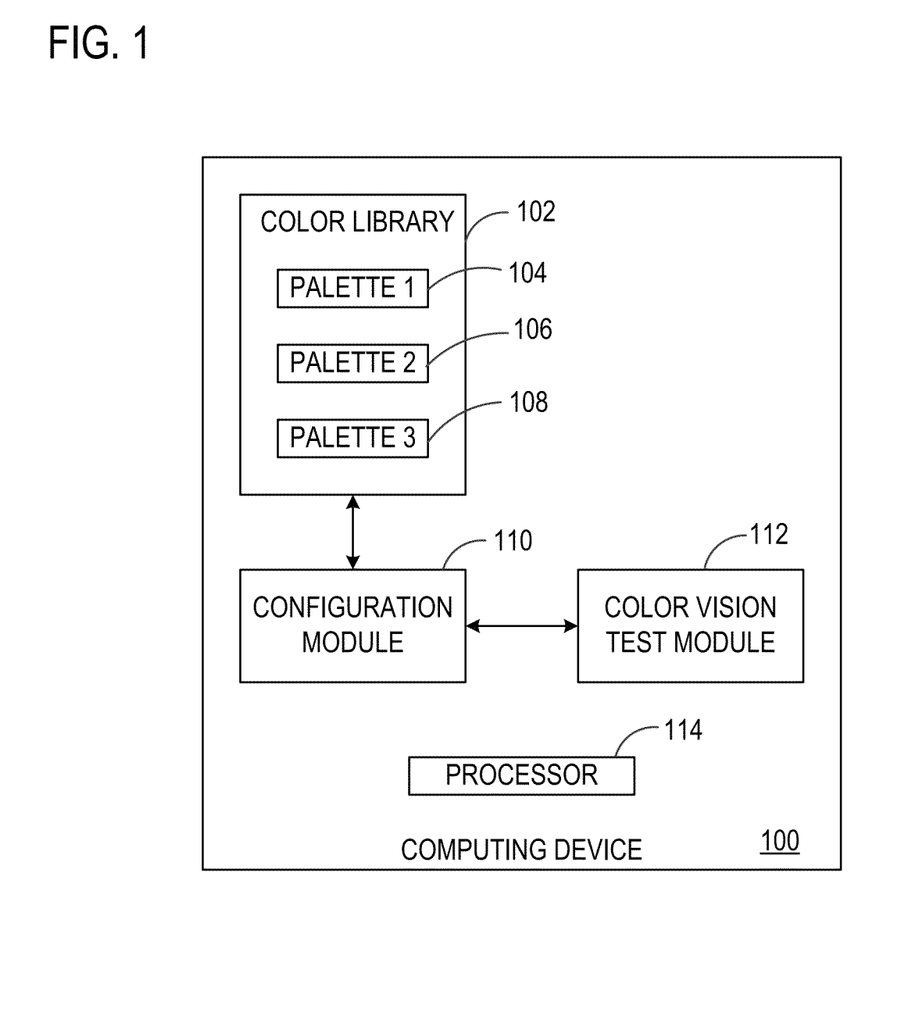
FIG. 1 is an example computing device capable of increasing accessibility of color vision impaired users to information presented on a display.

FIG. 1 illustrates a computing device 100. Computing device 100 includes a color library 102 storing a first color palette 104, a second color palette 106, and a third color palette 108. Color library 102 can be stored, for example, on a hard disk or computer memory. Although FIG. 1 illustrates three color palettes, additional color palettes are also possible. As used in this application, "color palette" refers to a group of possible colors that are available for use in graphical elements presented on a display. As used in this application, "graphical elements" includes window headers, themes, accents, dialog box headers, text, charts, graphs, data or personnel records, and other visual features which are typically displayed using colors. Images, including photographs, can also be graphical elements. The colors in first color palette 104, second color palette 106, and third color palette 108 can be specified in a variety of ways. Red-green-blue (RGB) color coding, for example, can be used to specify colors displayed on a screen such as a computer monitor, smart phone or tablet display, or other display that uses light to produce images.

Regardless of the coding scheme used, colors can be coded by specifying a contribution from each of a coding scheme's base components. In RGB color coding, red, green, and blue components are specified using, for example, Arabic or hexadecimal (hex) numbers. For example, a shade of red can be represented as red: 250, green: 44, blue: 66 or by the hex value FA2C42, in which FA is the red value, 2C is the green value, and 42 is the blue value. The higher value for the red component relative to the green and blue component indicates that the resulting color will appear closer to red than to blue or green for users without color vision impairment. Examples discussed in this application use RGB color codes, but other coding schemes such as cyan-magenta-yellow-black (CMYK), hue-saturation-value (HSV), hue-saturation-lightness (HSL), and so-called YUV, YCbCr, Y'CbCr, and YPbPr are also contemplated. For example, cyan-magenta-yellow-black (CMYK) color coding can be used to specify printed colors, and a corresponding CMYK color palette can be provided to aid color vision impaired users.

One of first color palette 104, second color palette 106, and third color palette 108 can be a default color palette designed for users who do not have a color vision impairment, and the other two of first color palette 104, second color palette 106, and third color palette 108 can be alternative color palettes designed for one or more types of color vision impairment. In some examples, color library 102 stores alternative color palettes while a default color palette is stored elsewhere. A configuration module 110 receives an indication that a user has a type of color vision impairment. Upon receiving the indication, configuration module 110 uses a processor 114 to alter graphical elements that use the default color palette by replacing the default color palette with an alternative color palette designed for the type of color vision impairment from which the user suffers.

The indication that a user has a type of color vision impairment can be obtained in several ways. In one example, descriptions of a plurality of color vision impairment types are presented to a user. The description of each of the plurality of color vision impairment types includes at least one of a scientific name, a common name, or a narrative description. A user input selecting one of the plurality of color vision impairment types is then received. This information can be provided to configuration module 110. In other examples, a color vision test module 112 is used. Color vision test module 112 presents at least one test capable of determining whether a user has a type of color vision impairment. In some examples, color vision test module 112 presents a single test capable of detecting multiple types of color vision impairment.

Although computing device 100 is shown as a single device with a single processor 114, the functionality implementing color library 102, configuration module 110, and color vision test module 112 can be distributed across a plurality of devices having a plurality of processors. For example, computing device 100 can be part of a cloud computing environment, and various portions of color library 102, configuration module 110, and color vision test module 112 can be implemented in a single server device in the cloud or be distributed across multiple devices in the cloud. Computing device 100 can also be a client computer.

In one example, computing device 100 includes computer memory storing instructions that, when executed by processor 114, perform all or some of the functionality in configuration module 110 and color vision test module 112. For example, instructions can be stored in memory for performing a method comprising receiving an indication that a user is color vision impaired and transmitting a request to select a color palette associated with a color vision impairment. In some examples, color library 102 is stored external to computing device 100, such as on another computing device. In a server implementation, a server computer can receive an indication that a user is color vision impaired and then transmit a request to select a color palette associated with a color vision impairment, regardless of where the color palette is stored.

Figure 2:
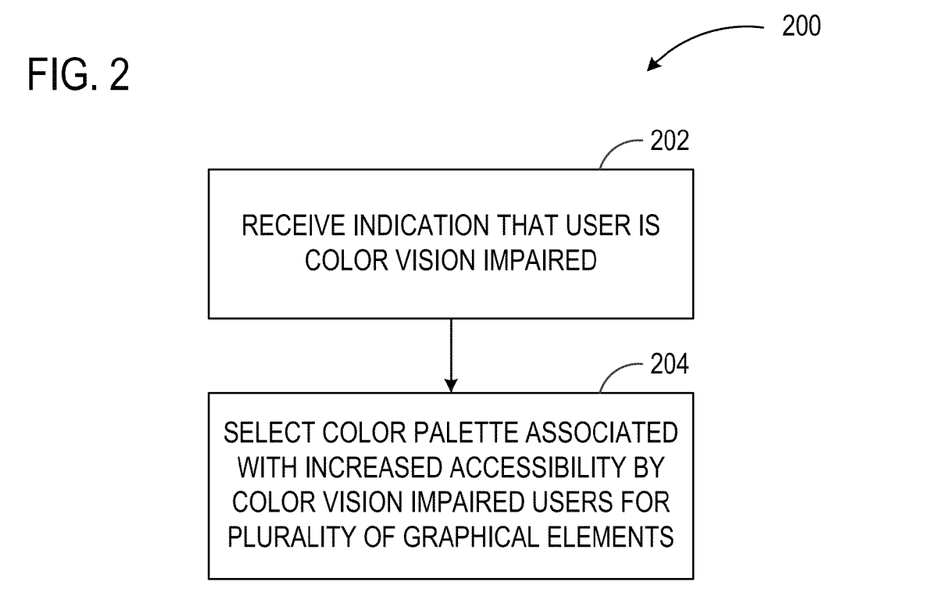
FIG. 2 is a flowchart of an example method of increasing accessibility of color vision impaired users to information presented on a display.

FIG. 2 illustrates a method 200 of increasing accessibility of color vision impaired users to information presented on a display. In process block 202, an indication is received that a user is color vision impaired. In some examples, method 200 further comprises providing a color vision impairment test, and the indication received in process block 202 may be received in response to the color vision impairment test. In other examples, the indication is received in response to a presentation of descriptions of a plurality of color vision impairment types. In process block 204, a color palette is selected for a plurality of graphical elements. The color palette is associated with increased accessibility by color vision impaired users. In some examples the plurality of graphical elements are initially displayed using a default color palette, and the color palette selected in process block 204 is an alternative color palette. The graphical elements can be related, such as multiple elements in a theme. For example, a particular application may have a theme such that windows, menus, graphs, charts, data records, etc., in the application use a particular combination of colors or variations of the particular combination of colors.

In some examples, method 200 further comprises presenting at least some of the plurality of graphical elements using the selected color palette. The presenting at least some of the plurality of graphical elements using the selected color palette can comprise using combinations of colors included in the selected color palette. The colors used in the combinations of colors have tone values that allow the colors to be distinguished by the user when the combinations are used. Tone can, for example, be reflected in color codes. In some examples, one or more base components (e.g., the red, blue, or green component) for each color used in a combination are different by a threshold amount. For example, two colors used together in a combination could have a red, blue, or green component with a difference of at least 20, 50, or some other threshold (on a 0-256 scale) to improve distinguishability. In another example, tones are measured based on calculation performed by an application such as Color Oracle, an open-source software application. Such calculations can be supplemented by a human perception test and/or user validation.

Figure 3A:
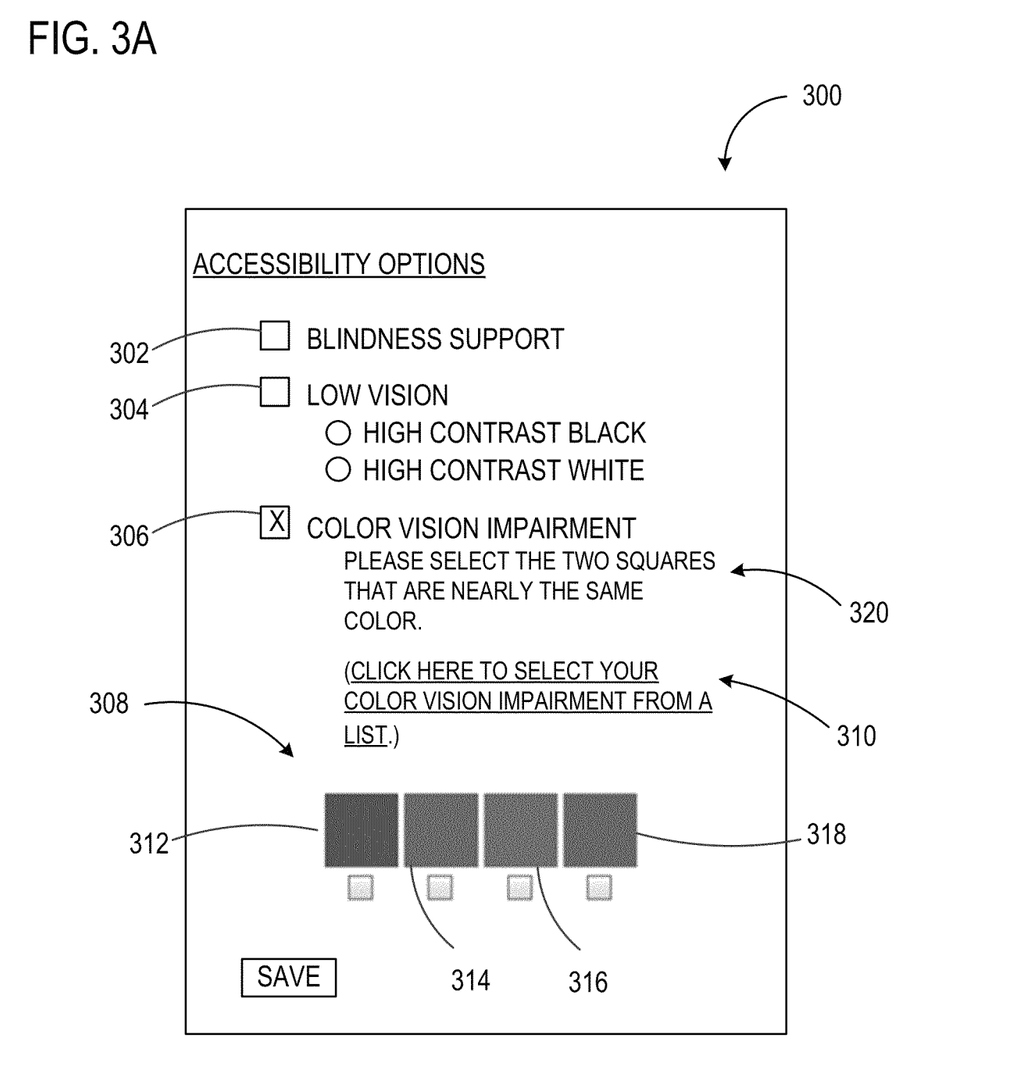
FIG. 3A is an example user interface including a single test capable of detecting multiple types of color vision impairment.
Figure 3B:
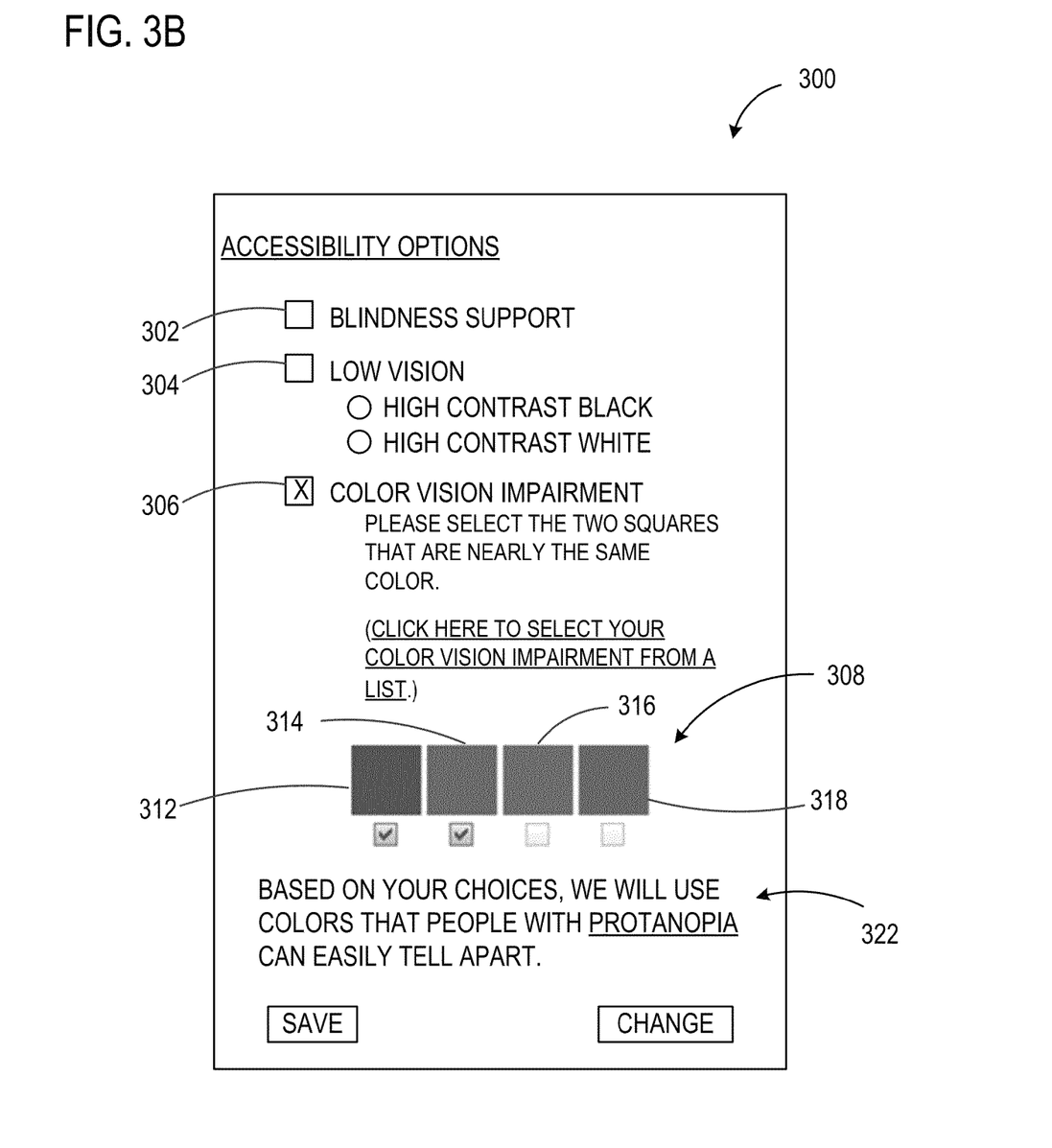
FIG. 3B is an example user interface in which, in response to a user selection of the two color samples in the test illustrated in FIG. 3A that appear closest to a same color, a type of color vision impairment is detected.

FIGS. 3A-3B illustrate an example user interface 300 that displays "Accessibility Options" selectable by a user. Option 302 is blindness support; option 304 is low vision support; and option 306 is accommodation for color vision impairment. In FIG. 3A, a user has selected option 306, which causes color vision impairment test 308 and color vision impairment description option 310 to be displayed. When selected, color vision impairment description option 310 presents descriptions (not shown) of a plurality of color vision impairment types. The description of each of the plurality of color vision impairment types can include at least one of a scientific name, a common name, or a narrative description.

Color vision impairment test 308 includes four color samples 312, 314, 316, and 318 arranged next to each other in a row. Instructions 320 presented with color samples 312, 314, 316, and 318 direct a user to "Please select the two squares that are nearly the same color." A user selection of two of color samples 312, 314, 316, and 318 that appear closest to a same color indicates a type of color vision impairment. In color vision impairment test 308, color sample 312 is a shade of black (R=88, G=85, B=69; hex 585545); color sample 314 is a shade of red (R=250, G=44, B=66; hex FA2C42); color sample 316 is a shade of green (R=39, G=158, B=73; hex 279E49); and color sample 318 is a shade of blue (R=26, G=140, B=159; hex 1A8C9F). In other examples, different colors are used and colors are presented in a different arrangement such as a column or grid. Selection of color samples 312 and 314 as the two colors that are nearly the same indicates the color vision impairment type is protonopia. Selection of color samples 314 and 316 as the two colors that are nearly the same indicates the user's color vision impairment type is deuteronopia. Selection of color samples 316 and 318 as the two colors that are nearly the same indicates the user's color vision impairment type is tritanopia. If color samples 312 and 318 are selected, an error message is presented. Display or monitor settings can have an effect on the appearance of color samples 312, 314, 316, and 318. In some examples, an instruction can be provided to return the display to default settings prior to selecting the two color samples that appear the same.

In FIG. 3B, a user has selected color samples 312 and 314 as appearing the same. As a result, a message 322 is presented stating "Based on your choices, we will use colors that people with Protanopia can easily tell apart." Thus, as a result of the user selection of color samples 312 and 314 indicating that the user has protanopia, at least some of a plurality of graphical elements, such as, for example, those included in an application user interface or theme, are presented using an alternative color palette having colors designed for users with protonopia. As shown in FIGS. 3A-3B, color vision impairment test 308 can be a test that a user selects from a menu such as an operating system or application options or settings menu. In some examples, color vision impairment test 308 can be presented to a user alternatively or additionally upon logging into a computing device or launching an application.

Color vision impairment test 308 is a single test capable of detecting multiple types of color vision impairment. That is, by following instructions 320 and selecting two of color samples 310, 312, 314, and 316, three different types of color vision impairment—protonopia, deuteronopia, and tritanopia—can be detected. In some examples, a multi-stage test can be used that presents subsets of color samples, for example two color samples at a time, and instructs the user to indicate whether the color samples appear the same. Such a multi-stage test can proceed from one stage to the next until a color vision impairment type is detected.

Many types of color vision impairment exist. Protanopia and deuteronopia are types of "red-green" color vision impairment, and tritanopia is a type of "blue-yellow" color vision impairment. In some examples, more than four color samples can be presented to detect additional types or sub-types of color vision impairment. In one example, a first color vision impairment test can present color samples that can be used to detect the most common types of color vision impairment first, and if a user elects to continue, a second color vision impairment test can be presented that includes color samples that can be used to detect less common types of color vision impairment.

Figure 4:
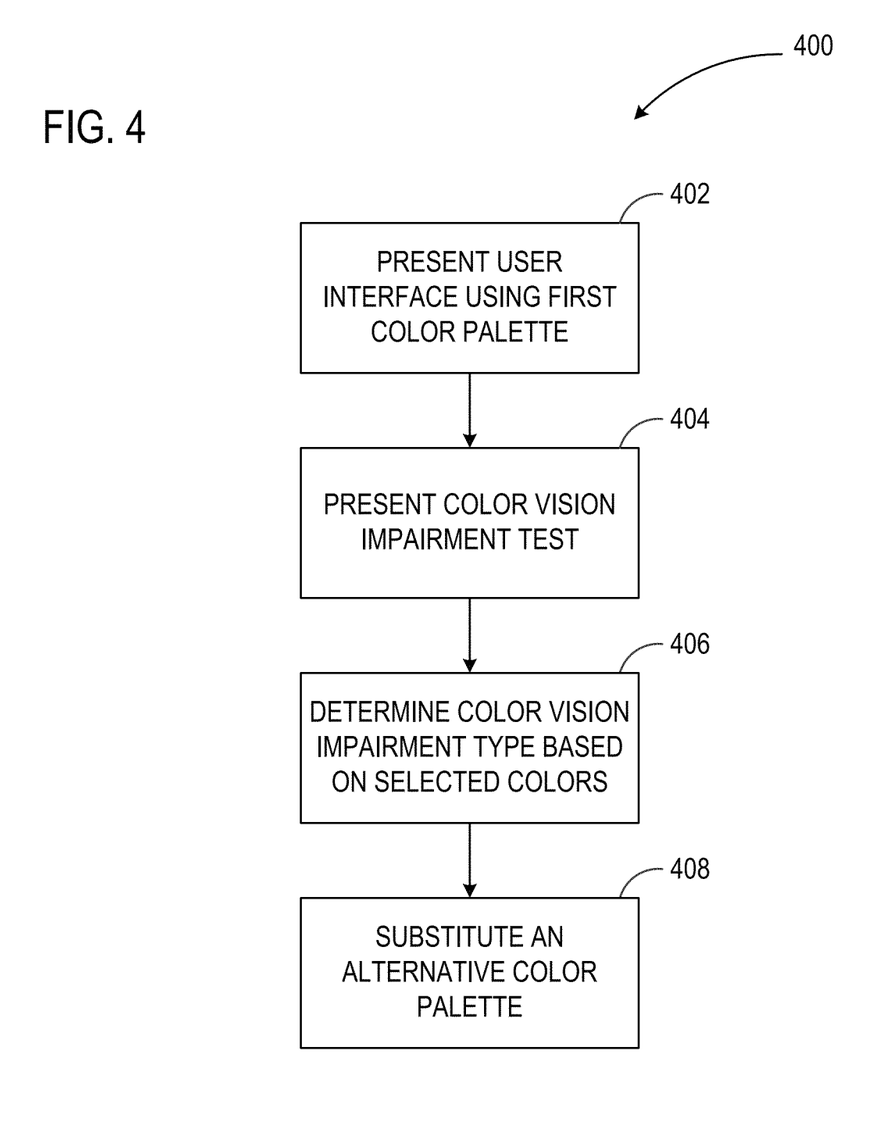
FIG. 4 is a flowchart of an example method of reconfiguring a user interface for increased accessibility to color vision impaired users.

FIG. 4 illustrates a method 400 for reconfiguring a user interface for increased accessibility to color vision impaired users. A user interface can include the graphical elements discussed above. In process block 402, a user interface having a first color palette is presented. A color vision impairment test capable of detecting multiple types of color vision impairment is presented in process block 404. The color vision impairment test can include instructions for a user to select two of a plurality of displayed color samples that appear to be a same color. The color samples can be arranged next to each other in a row, for example, as illustrated in FIGS. 3A-3B. In process block 406, a type of color vision impairment is determined based on the two selected color samples. In process block 408, an alternative color palette is substituted for the first color palette. The alternative color palate is designed for users having the determined type of color vision impairment. Thus, instead of incorporating colors from the first color palette, the user interface incorporates colors from the alternative color palate.

Figure 5:
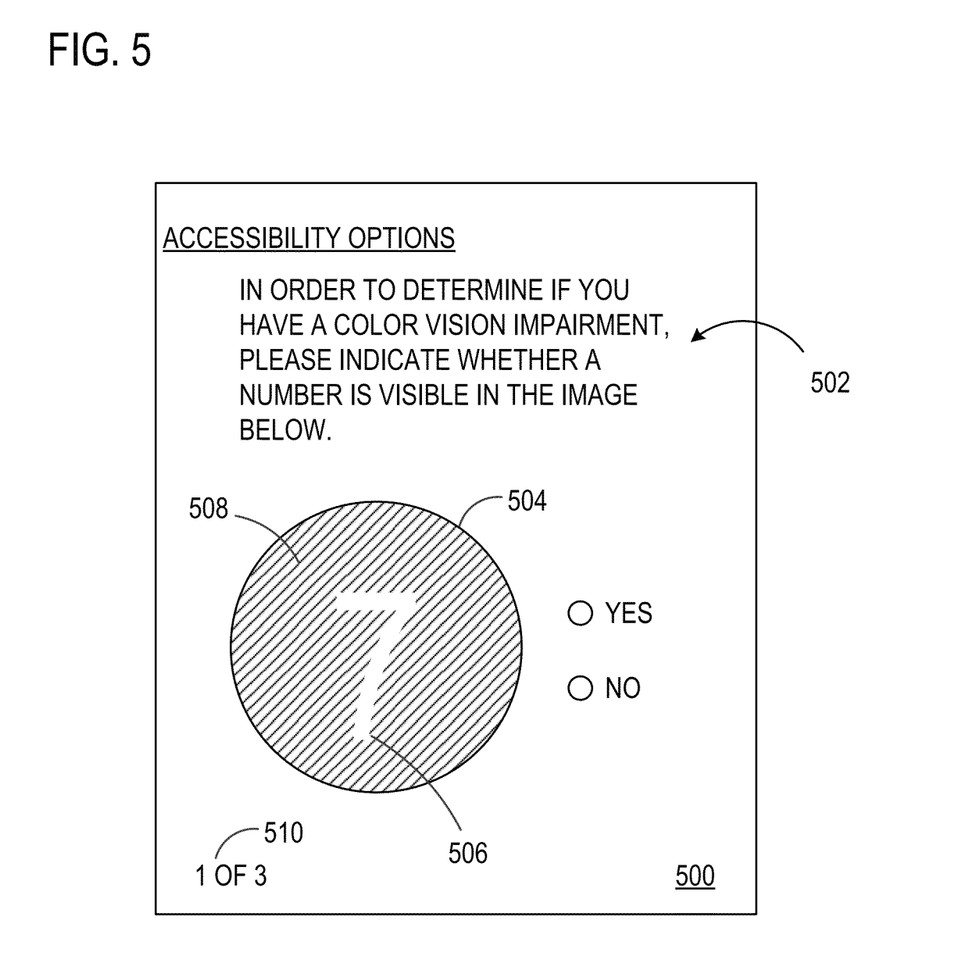
FIG. 5 is an example user interface including a test capable of detecting color vision impairment.

Color vision impairment tests other than those discussed with respect to FIGS. 3A-4 are also contemplated. FIG. 5 illustrates a user interface 500 in which instructions 502 direct a user, "In order to determine if you have a color vision impairment, please indicate whether a number is visible in the image below." Color vision impairment test 504 includes a number 506 surrounded by a background 508. The colors of the number 506 and the background 508 can be selected such that if a user cannot distinguish between the number 506 and the background 508, it is determined that the user has a type of color vision impairment. Color vision impairment test 504 can detect a single type of color vision impairment.

Page status indicator 510 shows that color vision impairment test 504 is the first of three tests in a series. Each test in the series can test for a different type of color vision impairment. In some examples, only one color vision impairment test is presented. In some examples, a single test that detects a single type of color vision impairment, for example a common type of color vision impairment, can be implemented to provide simplicity while still providing accessibility to a large number of users. Other tests, such as the Ishihara test, which includes a number and surrounding background made using an arrangement of differently sized colored circles, can also be used. A color vision impairment test can also be implemented using colors that detect degrees of color vision impairment. For example, a test can be presented such that severe but not minor color vision impairment will be detected in a user.

Color palettes can include any number of colors. Default color palettes designed for users without color vision impairment can include, for example, "web-safe colors" that can be produced without dithering. Web-safe colors can be used for web-based graphical elements such as cloud-based applications or for desktop-based graphical elements such as locally installed applications. The default color palette can also depend upon the language or protocol used to specify visual elements. For example, HTML 4 defines 16 colors. The Cascading Style Sheets (CSS) language defines 17 colors.

Figure 6:
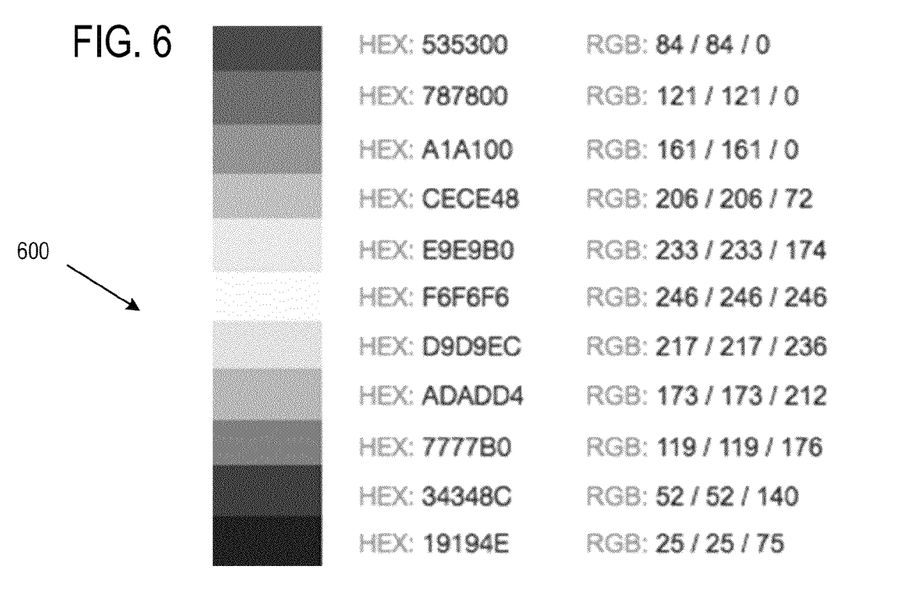
FIG. 6 is an example alternative color palette designed for users with deuteranopia or protanopia.

FIG. 6 is an alternative color palette 600 designed for users with deuteranopia or protanopia, both of which are types of red-green vision impairment. The colors in alternative color palette 600 tend to be more distinguishable by users with deuteranopia and protanopia. RGB color codes and corresponding hex values are listed for each color in alternative color palette 600. In some examples, an alternative color palette is designed for each of deuteranopia and protanopia. Additional alternative color palettes for sub-types of deuteranopia and protanopia are also contemplated.

Figure 7:
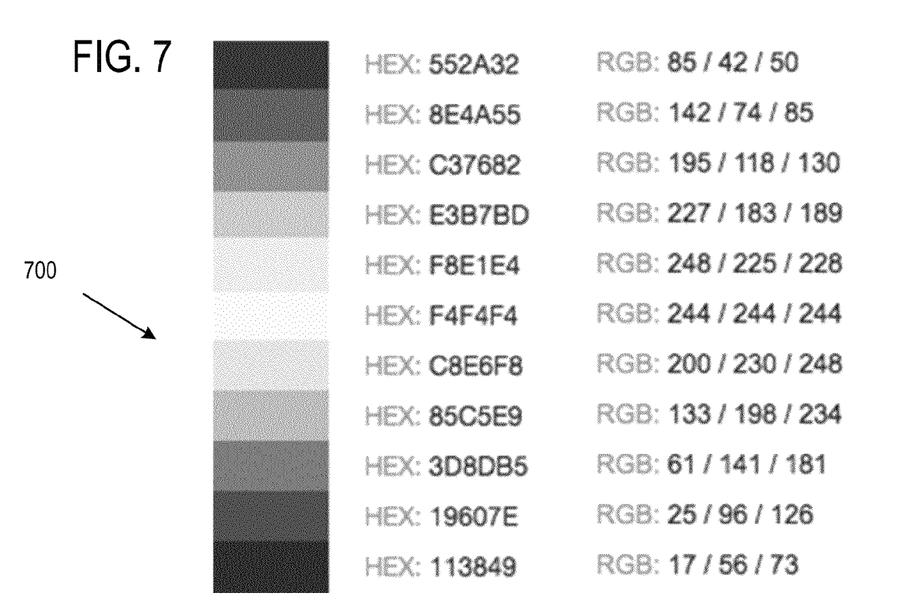
FIG. 7 is an example alternative color palette designed for users with tritanopia.

FIG. 7 is an alternative color palette 700 designed for users with tritanopia, which is a type of blue-yellow vision impairment. The colors in alternative color palette 700 tend to be more distinguishable by users with tritanopia. RGB color codes and corresponding hex values are listed for each color in alternative color palette 700.

Figure 8:
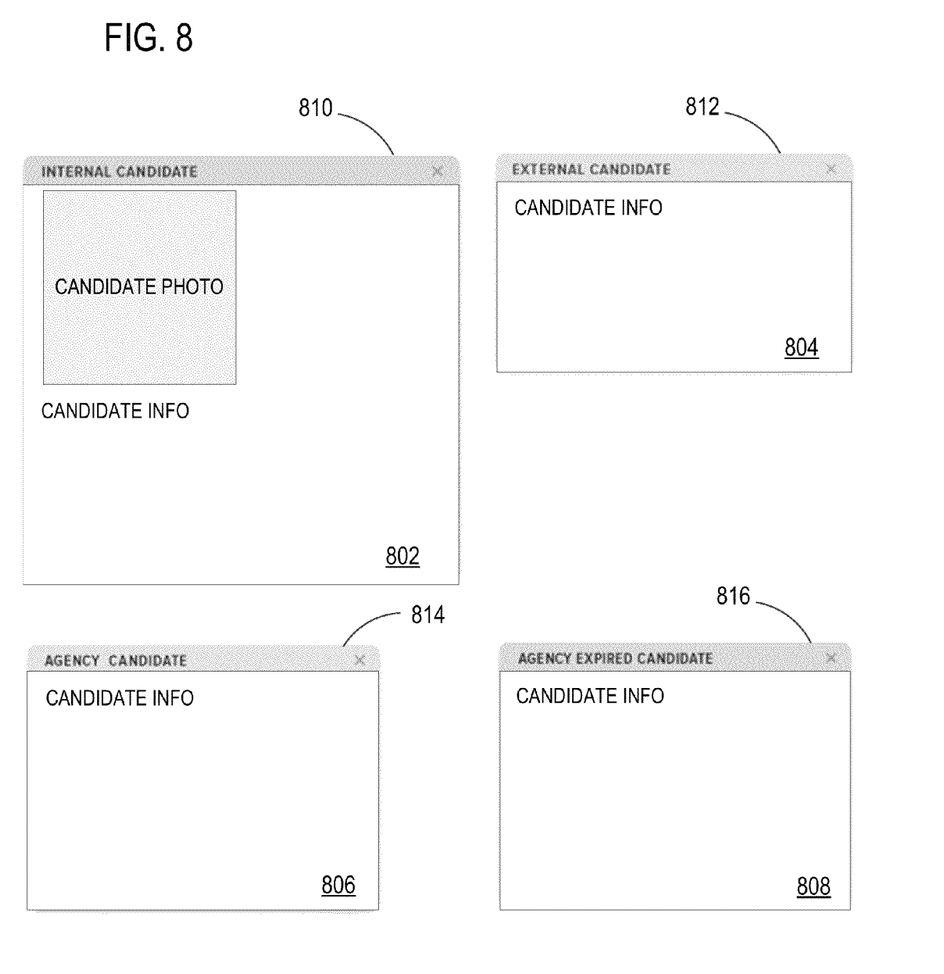
FIG. 8 is an example of graphical elements color-coded to convey meaning.
Figure 9:
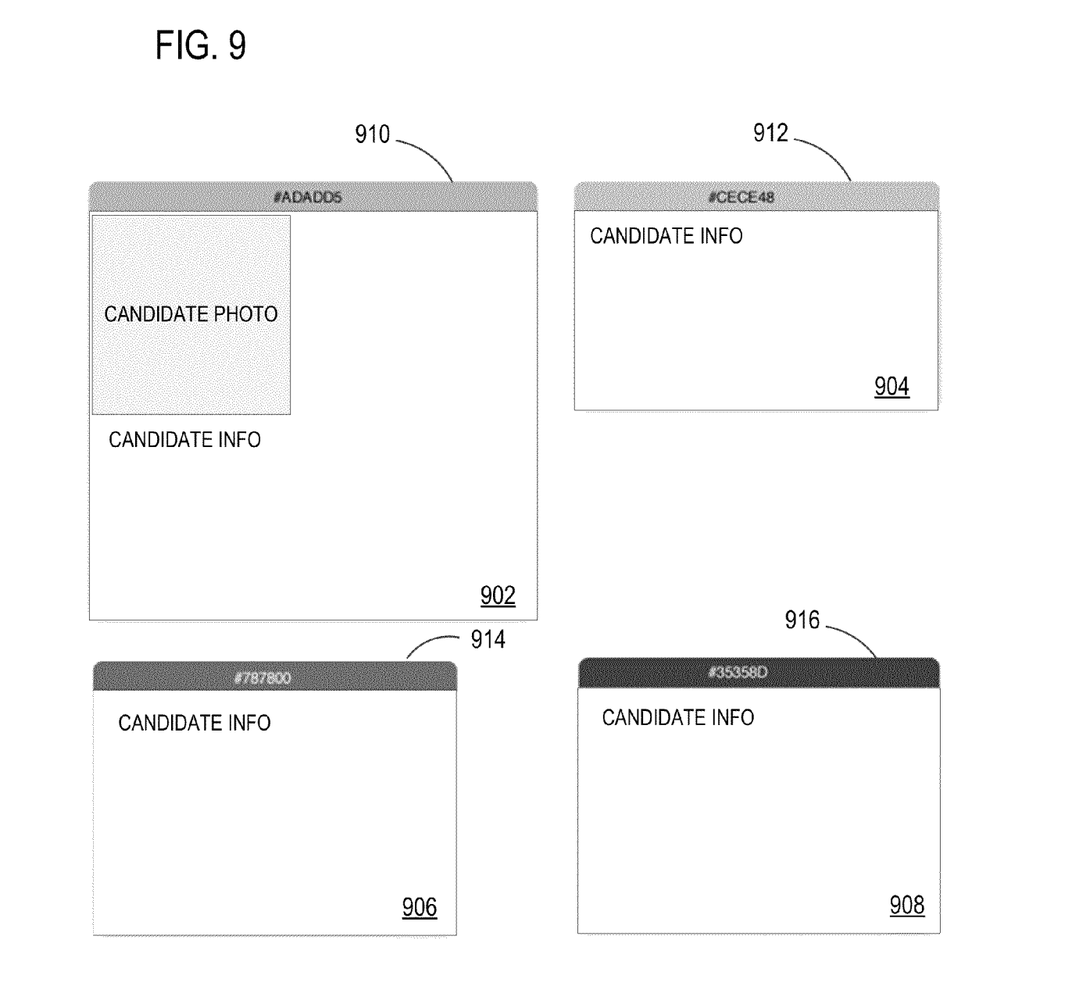
FIG. 9 illustrates the graphical elements of FIG. 8 using colors from an alternative color palette designed for users with deuteranopia.
Figure 10:
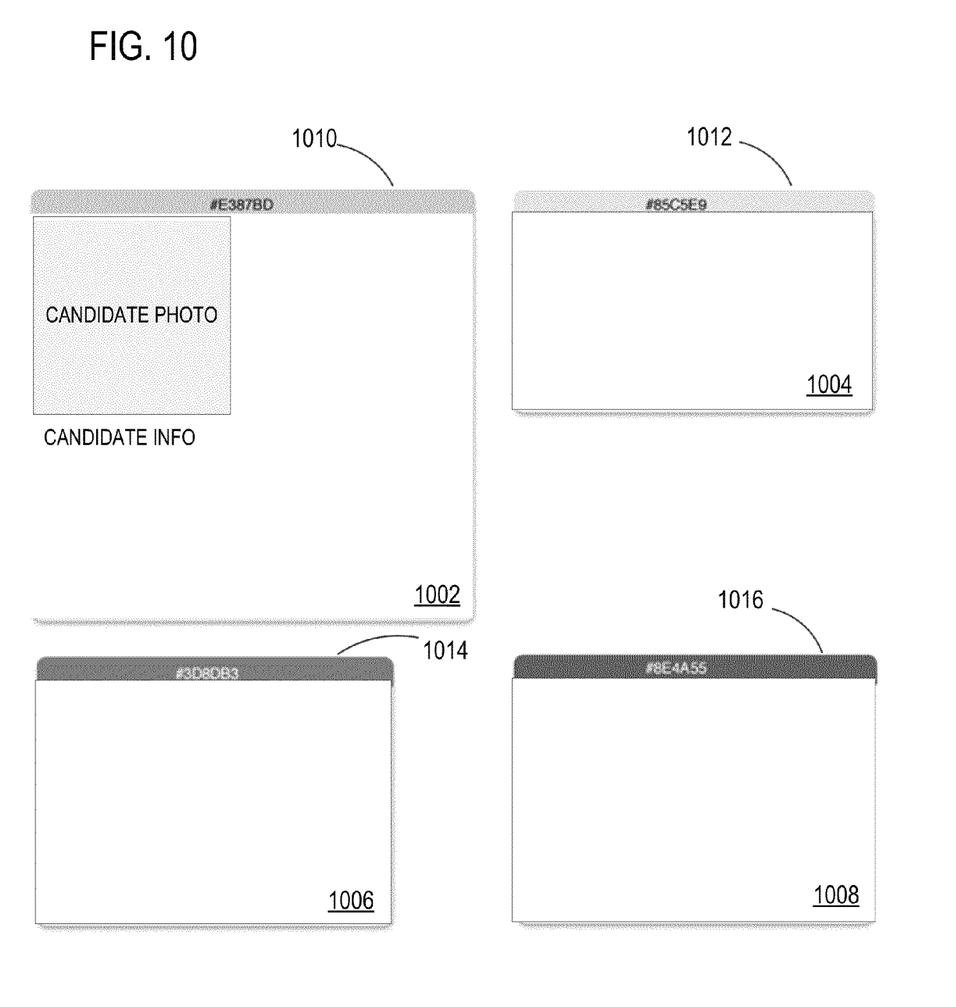
FIG. 10 illustrates the graphical elements of FIG. 8 using colors from an alternative color palette designed for users with tritanopia.

FIGS. 8-10 illustrate graphical elements presented using different color palettes in the context of a human resources software application. FIG. 8 illustrates candidate record windows 802, 804, 806, and 808. Candidate record windows 802, 804, 806, and 808 have color-coded headers 810, 812, 814, and 816 that indicate the source and/or status of the candidate. For example, header 810 of candidate record 802 is color coded a shade of blue and includes text to indicate the candidate is an internal candidate. While the included text in color-coded headers 810, 812, 814, and 816 provides some accessibility, color vision impaired users may not be able to take advantage of the color coding to quickly identify the source of candidates.

FIG. 9 illustrates candidate record windows 902, 904, 906, and 908 having color-coded headers 910, 912, 914, and 916. The colors used for color-coded headers 910, 912, 914, and 916 are selected from an alternative color palette (similar to alternative color palette 600 in FIG. 6) designed for users with deuteranopia. The text description (e.g. "internal candidate") is not shown in FIG. 9 for simplicity. The candidate record windows 902, 904, 906, and 908 are typically better suited for users with deuteranopia. Such users can more readily take advantage of color coding and will be more able to quickly understand the source and/or status of a candidate based on the header color of the candidate's record. The colors selected for use from an alternative color palette designed for users with deuteranopia are selected such that the tone values of the selected colors allow the colors to be distinguished by the user when the colors are used in combination. Other combinations of colors in the alternative color palette are possible, but some combinations include colors very close in appearance and are not used.

FIG. 10 illustrates candidate record windows 1002, 1004, 1006, and 1008 having color-coded headers 1010, 1012, 1014, and 1016. The colors used for color-coded headers 1010, 1012, 1014, and 1016 are selected from an alternative color palette (similar to alternative color palette 700 in FIG. 7) designed for users with tritanopia.

Example Computing Environment

Figure 11:
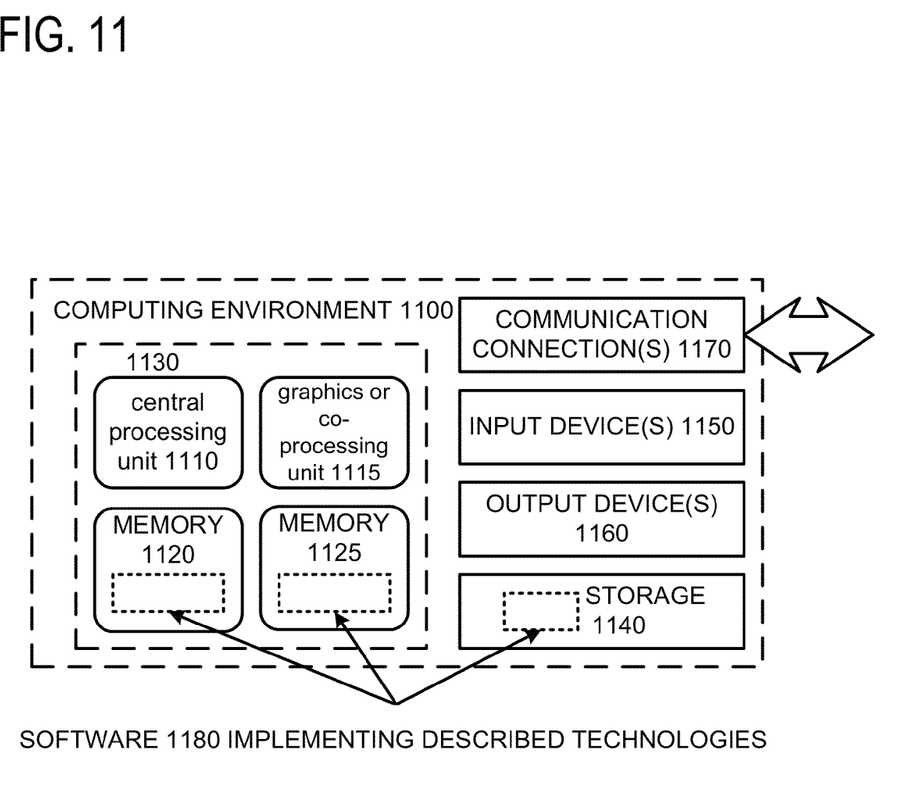
FIG. 11 illustrates an example computing environment suitable for implementing the examples disclosed herein.

FIG. 11 depicts a generalized example of a suitable computing environment 1100 in which the described innovations may be implemented. The computing environment 1100 is not intended to suggest any limitation as to scope of use or functionality, as the innovations may be implemented in diverse general-purpose or special-purpose computing systems. For example, the computing environment 1100 can be any of a variety of computing devices (e.g., desktop computer, laptop computer, server computer, tablet computer, media player, gaming system, mobile device, etc.)

With reference to FIG. 11, the computing environment 1100 includes one or more processing units 1110, 1115 and memory 1120, 1125. In FIG. 11, this basic configuration 1130 is included within a dashed line. The processing units 1110, 1115 execute computer-executable instructions. A processing unit can be a general-purpose central processing unit (CPU), processor in an application-specific integrated circuit (ASIC) or any other type of processor. In a multi-processing system, multiple processing units execute computer-executable instructions to increase processing power. For example, FIG. 11 shows a central processing unit 1110 as well as a graphics processing unit or co-processing unit 1115. The tangible memory 1120, 1125 may be volatile memory (e.g., registers, cache, RAM), non-volatile memory (e.g., ROM, EEPROM, flash memory, etc.), or some combination of the two, accessible by the processing unit(s). The memory 1120, 1125 stores software 1180 implementing one or more innovations described herein, in the form of computer-executable instructions suitable for execution by the processing unit(s). For example, color palettes, color test data, and related computer-executable instructions can be stored. In some cases, color palettes suitable for display and printing are stored, for example, as RGB and CMYK palettes, for users with and without color vision impairments.

A computing system may have additional features. For example, the computing environment 1100 includes storage 1140, one or more input devices 1150, one or more output devices 1160, and one or more communication connections 1170. An interconnection mechanism (not shown) such as a bus, controller, or network interconnects the components of the computing environment 1100. Typically, operating system software (not shown) provides an operating environment for other software executing in the computing environment 1100, and coordinates activities of the components of the computing environment 1100.

The tangible storage 1140 may be removable or non-removable, and includes magnetic disks, magnetic tapes or cassettes, CD-ROMs, DVDs, or any other medium which can be used to store information in a non-transitory way and which can be accessed within the computing environment 1100. The storage 1140 stores instructions for the software 1180 implementing one or more innovations described herein. For example, storage 1140 can include a color library, configuration module, and color vision test module such as those shown in FIG. 1. Modules contain computer-executable instructions.

The input device(s) 1150 may be a touch input device such as a keyboard, mouse, pen, or trackball, a voice input device, a scanning device, or another device that provides input to the computing environment 1100. For video encoding, the input device(s) 1150 may be a camera, video card, TV tuner card, or similar device that accepts video input in analog or digital form, or a CD-ROM or CD-RW that reads video samples into the computing environment 1100. The output device(s) 1160 may be a display, printer, speaker, CD-writer, or another device that provides output from the computing environment 1100.

The communication connection(s) 1170 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Example Operating Environment

Figure 12:
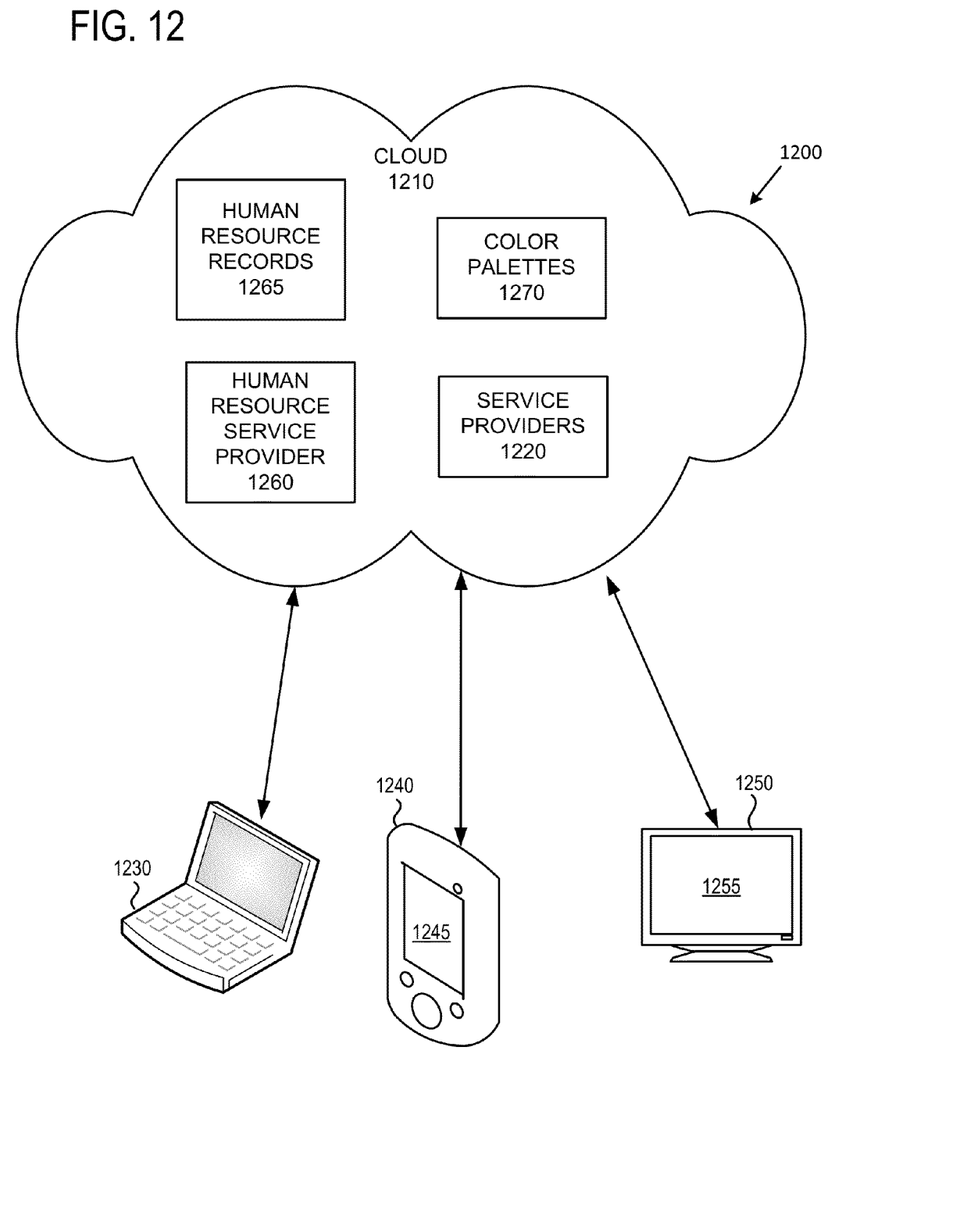
FIG. 12 illustrates an example cloud computing environment suitable for implementing the examples disclosed herein.

FIG. 12 illustrates a generalized example of a suitable implementation environment 1200 in which described embodiments, techniques, and technologies may be implemented.

In example environment 1200, various types of services (e.g., computing services) are provided by a cloud 1210. For example, the cloud 1210 can comprise a collection of computing devices, which may be located centrally or distributed, that provide cloud-based services to various types of users and devices connected via a network such as the Internet. The implementation environment 1200 can be used in different ways to accomplish computing tasks. For example, some tasks (e.g., processing user input and presenting a user interface) can be performed on local computing devices (e.g., connected devices 1230, 1240, 1250) while other tasks (e.g., storage of data to be used in subsequent processing) can be performed in the cloud 1210.

In example environment 1200, the cloud 1210 provides services for connected devices 1230, 1240, 1250 with a variety of screen capabilities. Connected device 1230 represents a device with a computer screen 1235 (e.g., a mid-size screen). For example, connected device 1230 could be a personal computer such as desktop computer, laptop, notebook, netbook, or the like. Connected device 1240 represents a device with a mobile device screen 1245 (e.g., a small size screen). For example, connected device 1240 could be a mobile phone, smart phone, personal digital assistant, tablet computer, or the like. Connected device 1250 represents a device with a large screen 1255. For example, connected device 1250 could be a television screen (e.g., a smart television) or another device connected to a television (e.g., a set-top box or gaming console) or the like. One or more of the connected devices 1230, 1240, and 1250 can include touchscreen capabilities. Touchscreens can accept input in different ways. For example, capacitive touchscreens detect touch input when an object (e.g., a fingertip or stylus) distorts or interrupts an electrical current running across the surface. As another example, touchscreens can use optical sensors to detect touch input when beams from the optical sensors are interrupted. Physical contact with the surface of the screen is not necessary for input to be detected by some touchscreens. Devices without screen capabilities also can be used in example environment 1200. For example, the cloud 1210 can provide services for one or more computers (e.g., server computers) without displays.

Services can be provided by the cloud 1210 through service providers 1220, or through other providers of online services (not depicted). For example, cloud services can be customized to the screen size, display capability, and/or touchscreen capability of a particular connected device (e.g., connected devices 1230, 1240, 1250).

In example environment 1200, the cloud 1210 provides the technologies and solutions described herein to the various connected devices 1230, 1240, 1250 using, at least in part, the service providers 1220. For example, the service providers 1220 can provide a centralized solution for various cloud-based services, including cloud-based human resource services. The service providers 1220 can manage service subscriptions for users and/or devices (e.g., for the connected devices 1230, 1240, 1250 and/or their respective users). Human resource service provider 1260 can also provide services to connected devices 1230, 1240, 1250. Human resource service provider 1260 can access and/or maintain human resource records 1265 and color palettes 1270. Color palettes 1270 can also be accessed by service providers 1220.

Connected devices 1230, 1240, and 1250 can display graphical elements, for example in conjunction with services provided by human resource service provider 1260. The graphical elements can be displayed using a first color palette located in color palettes 1270. Upon receiving a user input indicating that a user has a color vision impairment, at least some of the plurality of graphical elements can be presented using a second color palette in color palettes 1270 designed for users with the color vision impairment.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

Any of the disclosed methods can be implemented as computer-executable instructions stored on one or more computer-readable storage media (e.g., non-transitory computer-readable media, such as one or more optical media discs, volatile memory components (such as DRAM or SRAM), or nonvolatile memory components (such as flash memory or hard drives)) and executed on a computer. As should be readily understood, the term computer-readable storage media does not include communication connections, such as modulated data signals.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an Intranet, software applications, cable (including fiber optic cable), magnetic communications, electromagnetic communications (including RF, microwave, and infrared communications), electronic communications, or other such communication means.

The disclosed methods, apparatus, and systems should not be construed as limiting in any way. Instead, the present disclosure is directed toward all novel and nonobvious features and aspects of the various disclosed embodiments, alone and in various combinations and subcombinations with one another. The disclosed methods, apparatus, and systems are not limited to any specific aspect or feature or combination thereof, nor do the disclosed embodiments require that any one or more specific advantages be present or problems be solved.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims.

What is claimed is:

1. One or more computer-readable storage media storing instructions that, when executed by a computing device, perform a method of increasing accessibility of color vision impaired users to information presented on a display, the method comprising:
    providing a single color vision impairment test screen configured such that multiple types of color vision impairment can be identified based on the single color vision impairment test screen, the single color vision impairment test screen comprising a first color sample, a second color sample, a third color sample, and a fourth color sample, wherein the first, second, third, and fourth color samples are different colors;
    receiving a user response to the single color vision test screen indicating two of the first, second, third, or fourth color samples that appear to be a same color;
    based on the two indicated color samples, identifying a type of color vision impairment, wherein when the user response indicates the first and second color samples, a first type of color vision impairment is identified, wherein when the user response indicates the second and third color samples, a second type of color vision impairment is identified, and wherein when the user response indicates the third and fourth color samples, a third type of color vision impairment is identified; and
    selecting a color palette for a plurality of graphical elements, the color palette associated with increased accessibility by color vision impaired users having the identified type of color vision impairment.

2. The computer-readable storage media of claim 1, wherein the plurality of graphical elements includes at least one of a window header, theme, accent, dialog box header, text, chart, graph, or a personnel or other data record.

3. The computer-readable storage media of claim 1, wherein the identified type of color vision impairment is one of deuteranopia, protanopia, or tritanopia.

4. The computer-readable storage media of claim 1, wherein the method further comprises displaying descriptions of a plurality of color vision impairment types.

5. The computer-readable storage media of claim 4, wherein the displayed descriptions of the respective plurality of color vision impairment types include at least one of a scientific name, a common name, or a narrative description.

6. The computer-readable storage media of claim 1, wherein the method further comprises presenting at least some of the plurality of graphical elements using the selected color palette.

7. The computer-readable storage media of claim 6, wherein the presenting at least some of the plurality of graphical elements using the selected color palette comprises using combinations of colors included in the selected color palette, wherein the colors in the combinations of colors have tone values that allow the colors to be distinguished by users having the identified type of color vision impairment when the colors are used in the combinations of colors.

8. The computer-readable storage media of claim 1, wherein the single color vision test screen displays the first, second, third, and fourth color samples arranged in a row or a column.

9. The computer-readable storage media of claim 1, wherein the method is performed upon launching an application, and wherein the plurality of graphical elements for which the color palette is selected are associated with the application.

10. The computer-readable storage media of claim 1, wherein the first color sample is a shade of black, the second color sample is a shade of red, the third color sample is a shade of green, and the fourth color sample is a shade of blue, wherein when the user response indicates the first and second color samples, protanopia is identified, wherein when the user response indicates the second and third color samples, deuteranopia is identified, and wherein when the user response indicates the third and fourth color sample, tritanopia is identified.

11. One or more computing devices comprising:
a processor;
a color vision test module configured to, by the processor:
provide a single color vision impairment test screen configured to test for multiple different color vision impairment types, the single color vision impairment test screen comprising a first color sample, a second color sample, a third color sample, and a fourth color sample, wherein the first, second, third, and fourth color samples are different colors; and
upon receiving user feedback responsive to the single color vision impairment test screen indicating two of the first, second, third, or fourth color samples that appear to be a same color, determine that a user has a color vision impairment of the multiple different color vision impairment types, wherein when the user feedback indicates the first and second color samples, it is determined that the user has a first color vision impairment type, wherein when the user feedback indicates the second and third color samples, it is determined that the user has a second color vision impairment type, and wherein when the user feedback indicates the third and fourth color samples, it is determined that the user has a third color vision impairment type; and
a configuration module configured to, by the processor:
receive an indication that the user has the color vision impairment; and
select an alternative color palate for a plurality of graphical elements, the alternative color palette associated with the color vision impairment.

12. The one or more computing devices of claim 11, wherein the configuration module is further configured to generate the plurality of graphical elements for display using the alternative color palette.

13. The one or more computing devices of claim 11, wherein the one or more computing devices are user devices.

14. The one or more computing devices of claim 11, wherein the color vision test module provides the single color vision impairment test screen when an application is launched, and wherein the plurality of graphical elements for which the alternative color palette is selected are associated with the application.

15. The one or more computing devices of claim 11, wherein the first color sample is a shade of black, the second color sample is a shade of red, the third color sample is a shade of green, and the fourth color sample is a shade of blue, and wherein the first color vision impairment type is protanopia, the second color vision impairment type is deuteranopia, and the third color vision impairment type is tritanopia.

16. A computer-implemented method of reconfiguring a user interface for increased accessibility to color vision impaired users, the method comprising:
presenting a user interface having a first color palette;
presenting (i) a group of color samples, the group of color samples configured to simultaneously test for multiple different types of color vision impairment, the group of color samples comprising a black sample, a red sample, a green sample, and a blue sample, and (ii) instructions for a user to select two of the black, red, green, or blue color samples that appear to be a same color;
receiving a user selection of two of the black, red, green, or blue color samples, wherein a user selection of the black and red color samples indicates that the user has protanopia, a user selection of the red and green color samples indicates that the user has deuteranopia, and a user selection of the green and blue color samples indicates that the user has tritanopia;
determining a type of color vision impairment based on the two selected color samples; and
substituting an alternative color palette for the first color palette, the alternative color palette being designed for users having the determined type of color vision impairment.

17. The computer-implemented method of claim 16, further comprising prior to presenting the user interface having the first color palette, launching an application, wherein the alternative color palette is substituted for the first color palette for graphical elements associated with the application.

18. The computer-implemented method of claim 16, wherein: the black color sample is represented as red=88, green=85, and blue=69; the red sample is represented as red=250, green=44, and blue=66; the green color sample is represented as red=39, green=158, and blue=73; and the blue color sample is represented as red=26, green=140, and blue=159.

\* \* \* \* \*